US012616794B2

(12) United States Patent
Rivier et al.

(10) Patent No.: US 12,616,794 B2
(45) Date of Patent: May 5, 2026

(54) MEDICAL CONTAINER, SUCH AS A PRE-FILLABLE OR PREFILLED SYRINGE, COMPRISING A RFID TAG FOR REMOTE IDENTIFICATION OF SAID MEDICAL CONTAINER

(71) Applicants:Becton Dickinson France, Le Pont de Claix (FR); Becton, Dickinson and Company, Franklin Lakes, NJ (US)

(72) Inventors: Cédric Rivier, Voreppe (FR); Nicolas Euvrard, Plainsboro, NJ (US)

(73) Assignees: Becton Dickinson France, Le Pont de Claix (FR); Becton, Dickinson and Company, Franklin Lakes, NJ (US)

( * ) Notice: Subject to any disclaimer, the term of this patent is extended or adjusted under 35 U.S.C. 154(b) by 645 days.

(21) Appl. No.: 18/018,113

(22) PCT Filed: Jul. 26, 2021

(86) PCT No.: PCT/EP2021/070879
§ 371 (c)(1),
(2) Date: Jan. 26, 2023

(87) PCT Pub. No.: WO2022/023281
PCT Pub. Date: Feb. 3, 2022

(65) Prior Publication Data
US 2023/0256172 A1     Aug. 17, 2023

(30) Foreign Application Priority Data
Jul. 27, 2020    (EP) ..................................... 20305859

(51) Int. Cl.
*A61M 5/31* (2006.01)
*A61B 90/98* (2016.01)
(Continued)

(52) U.S. Cl.
CPC ........... *A61M 5/3134* (2013.01); *A61B 90/98* (2016.02); *A61M 5/158* (2013.01); *A61M 5/329* (2013.01);
(Continued)

(58) Field of Classification Search
CPC .... A61M 5/3134; A61M 5/158; A61M 5/329; A61M 5/34; A61M 2205/35; A61M 2205/60; A61B 90/98
See application file for complete search history.

(56) References Cited

U.S. PATENT DOCUMENTS 8,211,057 B2    7/2012  Nemoto et al.
9,070,069 B2    6/2015  Sinnett
(Continued)

FOREIGN PATENT DOCUMENTS

CN            101115515 A        1/2008
CN            103068598 A        4/2013
(Continued)

*Primary Examiner* — Tasnim Mehjabin Ahmed
(74) *Attorney, Agent, or Firm* — The Webb Law Firm

(57)                ABSTRACT
This medical container includes a barrel defining a reservoir for containing a medical product, and a needle extending in a barrel channel provided at a distal end of the barrel so as to establish a fluid communication between the reservoir and the needle. The medical container further includes a RFID on-metal (ROM) tag, said RFID on-metal tag being located at least partly inside the barrel channel and having an antenna extending along the needle.

8 Claims, 2 Drawing Sheets

(51) Int. Cl.
    A61M 5/158      (2006.01)
    A61M 5/32       (2006.01)
    A61M 5/34       (2006.01)

(52) U.S. Cl.
    CPC ........... A61M 5/34 (2013.01); A61M 2205/35
               (2013.01); A61M 2205/60 (2013.01)

(56)            References Cited

U.S. PATENT DOCUMENTS

| | | | |
|---|---|---|---|
| 9,595,100 | B2 | 3/2017 | Wong et al. |
| 11,160,930 | B2 | 11/2021 | Roedle |
| 11,744,755 | B2 | 9/2023 | Augustine et al. |
| 2009/0156931 | A1* | 6/2009 | Nemoto ............ A61M 5/14546 |
| | | | 600/432 |
| 2019/0201631 | A1* | 7/2019 | Miller ................... A61M 5/162 |
| 2019/0217011 | A1* | 7/2019 | Roedle .................... A61J 1/065 |
| 2019/0328485 | A1 | 10/2019 | Bauss et al. |
| 2021/0204936 | A1* | 7/2021 | Meyer ................... A61B 90/98 |

FOREIGN PATENT DOCUMENTS

| | | | |
|---|---|---|---|
| CN | 107122815 | A | 9/2017 |
| EP | 1932556 | A1 | 6/2008 |
| JP | 2004192114 | A | 7/2004 |
| JP | 2013537782 | A | 10/2013 |
| RU | 2698022 | C2 | 8/2019 |
| WO | 2017157784 | A1 | 9/2017 |
| WO | 2019222139 | A1 | 11/2019 |

* cited by examiner

MEDICAL CONTAINER, SUCH AS A PRE-FILLABLE OR PREFILLED SYRINGE, COMPRISING A RFID TAG FOR REMOTE IDENTIFICATION OF SAID MEDICAL CONTAINER

CROSS-REFERENCE TO RELATED APPLICATIONS

This application is the United States national phase of International Application No. PCT/EP2021/070879 filed Jul. 26, 2021, and claims priority to European Patent Application No. 20305859.9 filed Jul. 27, 2020, the disclosures of which are hereby incorporated by reference in their entirety.

BACKGROUND OF THE INVENTION

Field of the Invention

The present invention relates to a medical container, such as a pre-fillable or prefilled syringe, comprising a RFID tag linked to a needle.

Description of Related Art

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a medical container of the invention, and the "proximal direction" is to be understood as meaning the opposite direction to said direction of injection, that is to say the direction towards the user's hand holding a container as for an injection operation.

Medical injection devices, for example pre-fillable or prefilled syringes, usually comprise a hollow body or barrel forming a container for a medical product. This body comprises a distal end, optionally provided with a needle, and a proximal end, usually provided with a flange.

There is an increasing need for individual traceability of the medical containers, such as medical injection devices, from the manufacturing process until the final labeling, the final use or the disposal of said medical containers.

It is known, for example, from WO2017157784, a receptacle having a cylindrical lateral surface surrounded by a sequence of printed machine-readable unique identifier codes. These printed unique identifier codes allow tracking and tracing of each receptacle along a supply chain. However, these unique identifier codes are printed on an external side of the receptacle so that they may be removed or damaged, for example, during handling or use of the receptacle. Moreover, the unique identifier codes cover a portion of the receptacle so that they may have an impact on a user visual inspection process. Finally, an inkjet printer is used to print the identifier codes on the external side of the receptacle. However, this printing method, using ink, may lead to a risk of contamination of the receptacle. Moreover, one may not have access to these printed unique identifier codes when the receptacle is put, for example, in a sealed packaging.

SUMMARY OF THE INVENTION

In this context, an object of the present invention is to provide a device that alleviates the above-mentioned drawbacks by allowing an efficient individual identification of a medical container with no impact on visual inspection, with few or no risks of being removed or damaged, and with a limited impact on the manufacturing process.

A first aspect of the invention is a medical container comprising a barrel defining a reservoir for containing a medical product, and a needle extending in a barrel channel provided at a distal end of the barrel so as to establish a fluid communication between the reservoir and the needle, wherein the medical container further comprises a RFID on-metal (ROM) tag, said RFID on-metal (ROM) tag being located at least partly inside the barrel channel and having an antenna extending along the needle.

The invention therefore allows individual traceability of each medical container from the manufacturing process to the final use of the medical container. Besides, the ROM tag is well protected from removal or external damage that may occur due to the packaging, storing distribution or the use of the medical container. Additionally, the ROM tag is not into contact with the medical product contained inside the medical container. Furthermore, the ROM tag does not hinder the end user visual inspection. The ROM tag also does not provide any additional thickness to the medical container. Additionally, the antenna extending along the needle permits to increase the reading/writing distance since the metal needle is being used as an antenna transmitter.

In an embodiment, the antenna is spiral-shaped and helically wound up around the needle.

In an embodiment, the RFID on-metal (ROM) tag is a Ultra High Frequency RFID on-metal (UHF-ROM) tag. Preferably, the antenna comprises two separate legs each connected to the chip and forming two non-jointed coils around the needle. The above features enable to increase the reading/writing distance.

In an embodiment, the medical container comprises an adhesive for securing the needle to the barrel channel, and the RFID on-metal (ROM) tag is embedded into said adhesive. This permits to protect the ROM tag from the outside environment and to further prevent any contact with the skin of the end user during an injection operation.

In an embodiment, the antenna extends along a predetermined needle portion, said predetermined needle portion having a length of at least 2 mm and said predetermined needle portion corresponding at most to the whole needle portion that is contained inside the barrel channel.

In an embodiment, the antenna is located proximal to a chip of the RFID on-metal (ROM) tag.

Another aspect of the invention is a method for manufacturing a medical container including the above-described features, comprising the steps of:

i. attaching the RFID on-metal (ROM) tag to the needle;
ii. positioning the needle into the barrel channel;
iii. securing the needle inside the barrel channel;
iv. storing a Unique Device Identifier (UDI) into the ROM tag for identification of the medical container.

It is contemplated that the above steps (i) and (ii) may occur in any appropriate order. In an embodiment, step (i) may occur before step (ii). In an alternative embodiment, step (ii) may occur before step (i).

Preferably, the step (iii) occurs after steps (i) and (ii).

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1:
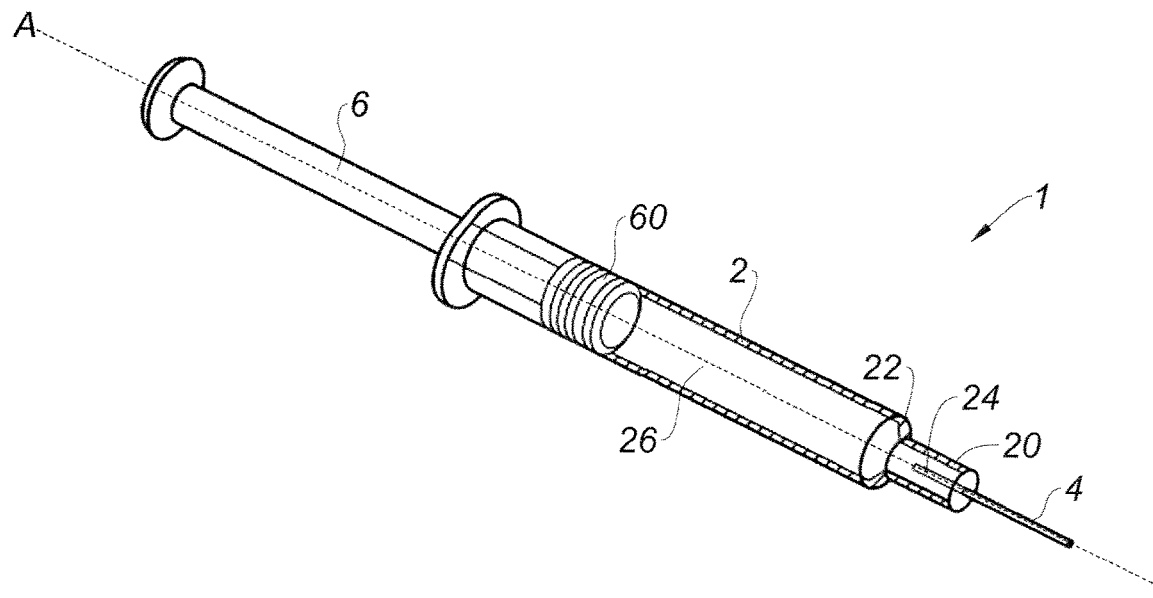
FIG. 1 is perspective view of a standard medical container.

With reference to FIG. 1 is shown a medical container 1 such as a pre-fillable or prefilled syringe. The medical container 1 comprises a cylindrical barrel 2 defining a reservoir 26 for containing a medical product, such as a medical composition. The barrel 2 extends along a longitudinal axis A and has a distal end that may be in the form of a longitudinal distal tip 20. The tip may extend distally from a distal shoulder 22 of the barrel 2. The distal tip 20 defines a barrel channel 24 configured to receive a needle 4 in order to establish a fluid communication between the reservoir 26 and the needle. The medical container 1 also includes a plunger rod 6 having a plunger 60 at a distal end thereof so as to expel the medical product contained in the reservoir 26 through the needle. The barrel 2 may be made of a glass or a plastic material. In an alternate embodiment (not shown), the needle 4 may be secured to a needle hub that is connected to the distal end 20 of the barrel 2; the needle hub may be threaded to an adaptor mounted onto the distal end 20 of the barrel 2.

Figure 2:
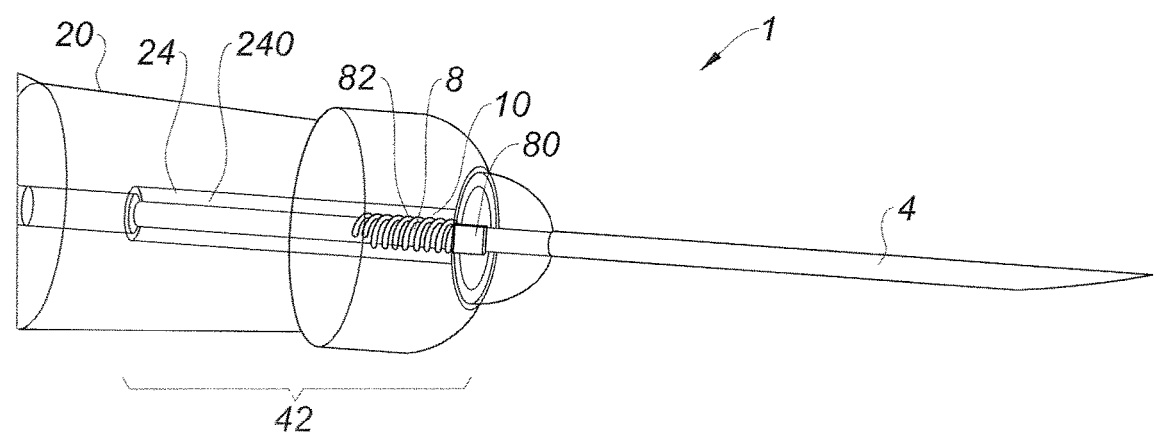
FIG. 2 is a semi-transparent view of a medical container according to an embodiment of the invention.
Figure 3:
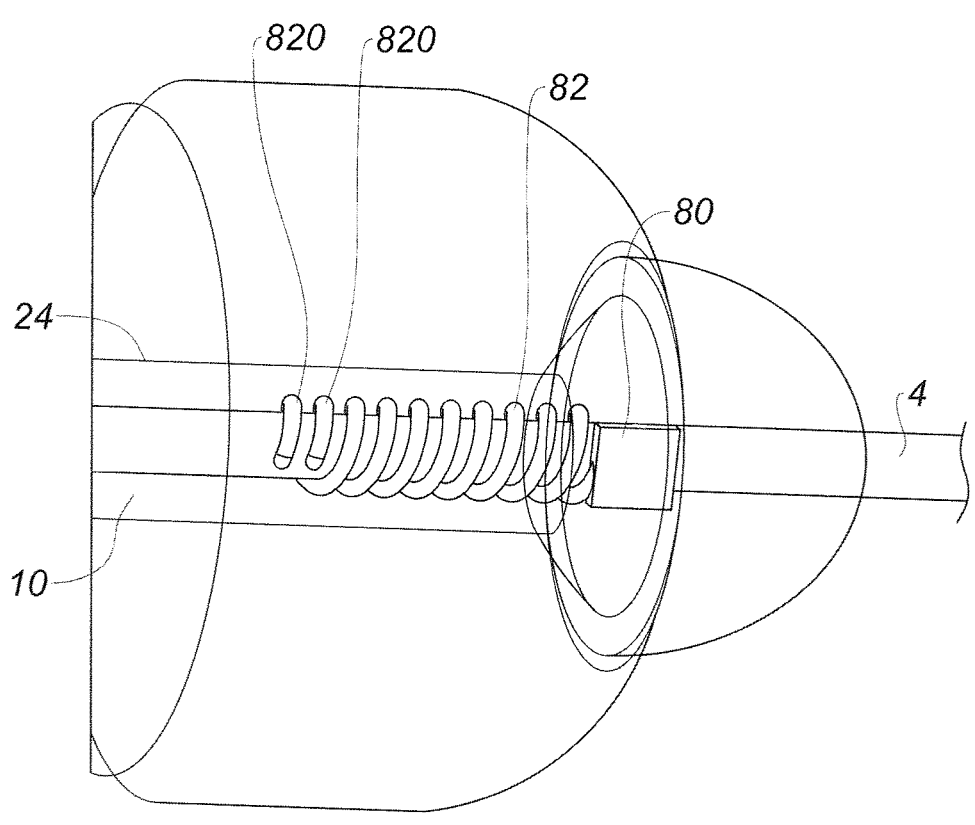
FIG. 3 is a detail of FIG. 2.

With reference to FIGS. 2 to 3, the medical container 1 of the invention includes a ROM (RFID on-metal) tag 8 attached to the needle 4 and fully or at least partly located inside the barrel channel 24, such that the ROM tag 8 is mainly not visible to an end-user and protected from the outside environment. A RFID on metal (ROM) tag 8 is a radio-frequency identification (RFID) tag 8 configured to perform a predetermined function when attached near a metal object. More specifically, the ROM tag 8 is arranged in the gap 240 defined between an outer surface of the needle 4 and an inner surface of the barrel channel 24.

The ROM tag 8 is attached to the needle 4 by means of an adhesive 10. In a preferred embodiment, the needle 4 is firstly inserted in the barrel channel 24. The ROM tag 8 is then inserted in the barre channel 24, positioned near the needle 4 and the ROM tag 8 is fixed to the needle 4 by means of a glue material that also secures the needle 4 to the barrel 2, said glue material filling the gap 240 formed between the needle 4 and the inner wall of the barrel channel 24.

In another embodiment, the ROM tag 8 is fixed to the needle 4 before insertion of the needle 4 inside the barrel channel 24. The ROM tag 8 may be located on a substrate, such as a ceramic or a plastic substrate, having an adhesive layer and said substrate is fixed on an outer surface of the needle 4 by means of said adhesive layer. Then the needle 4 is secured to the barrel 2 into the barrel channel 24 by means of a glue material filling the gap 240.

It is contemplated that the ROM tag 8 preferably does not contact the needle 4, i.e. is separated from the needle 4 by the substrate and/or the adhesive 10.

In yet another embodiment, the ROM tag 8 is firstly fixed to the needle 4 by welding a portion of the antenna 82 to the needle 4. Then, the needle 4 is inserted inside the barrel channel 24 and secured to the barrel 2 by means of a glue material filling the gap 240.

It is contemplated that the glue material that secures the needle 4 to the barrel 2 preferably fully embeds the ROM tag 8, thereby preventing any contact between the ROM tag 8 and the outside environment.

Figure 4:
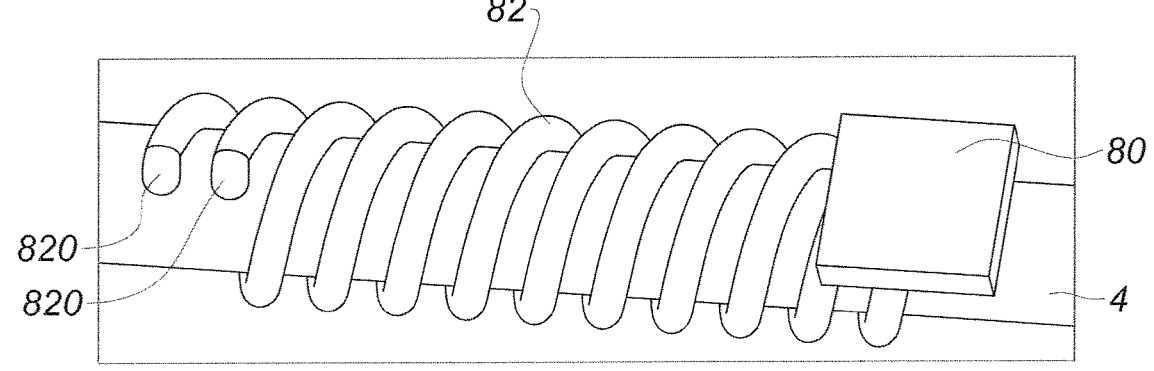
FIG. 4 is a perspective view of a ROM tag positioned onto the needle of a medical container according to the invention.

As visible on FIGS. 2 to 4, the ROM tag 8 includes a chip 80 and an antenna 82. The chip 80 is configured to store a Unique Device Identifier (UDI). The UDI allows remote identification of the medical container 1 from the manufacturing process until the final labeling, the final use or the disposal of the medical container 1.

The antenna 82 longitudinally extends along the needle 4 such that the needle 4 becomes an extension of said antenna 82, thereby improving the reading range of the ROM tag 8. Alternatively, the antenna 82 extends in a proximal direction from the chip 80. With reference for instance to FIG. 3, the antenna 82 may have a spiral shape and may be wound up around the needle 4 in order to increase the reading range. Preferably, the antenna 82 extends over a predetermined needle portion 40, said predetermined needle portion 40 having a length of at least 2 mm. At most, the antenna 82 extends all along the needle portion 42 that is located inside the barrel channel 24.

The ROM tag 8 may be a Low Frequency (about 30-300 kHz) ROM (LF-ROM) tag 8, a High Frequency (about 3-30 MHz) ROM (HF-ROM) tag 8 or, preferably, an Ultra High Frequency (about 400-1000 MHz) ROM (UHF-ROM) tag 8. A RFID reader can for example read the LF-ROM tag 8 at a distance up to about 10 cm, the HF-ROM tag 8 at a distance of about one meter and the UHF-ROM tag 8 at a distance of about fifteen meters.

With reference to FIG. 4, when the ROM tag 8 is an Ultra High Frequency ROM tag 8, the antenna 82 may include two separate legs 820 each connected to the chip 80 and forming two non-jointed coils around the needle. Both legs 820 preferably extend in a proximal direction from the chip 80.

The dimensions of the ROM tag 8 may be such that the ROM tag 8 is very compact and does not add thickness to the medical container 1. For instance, the antenna 82 diameter may be no more than 0.4 mm, for instance about 0.2 mm. The chip 80 dimension may be about 1 mm×0.5 mm×0.1 mm (length×width×thickness).

The invention also relates to a method for manufacturing the above-described medical container 1.

This method comprises a step (i) of positioning the ROM tag 8 onto the needle.

This step (i) may occur after insertion of the needle 4 in the barrel channel 24; a glue material then fills the gap 240 in order to secure the ROM tag 8 to the needle 4 and the needle 4 to the barrel 2.

Alternatively, the step (i) may occur before insertion of the needle 4 in the barrel channel 24. For example, the ROM tag 8 is positioned on a tubular plastic or ceramic substrate. This substrate is placed around the needle. In an embodiment, the substrate has an adhesive layer so as to be directly fixed onto the needle. In another embodiment, the substrate is devoid of any adhesive layer and may be later fixed to the needle 4 by the glue material that fills the barrel channel 24 to secure the needle 4 to the barrel 2. In yet another example, a portion of the antenna 82 is welded to the needle 4 before the needle 4 is inserted in the barrel channel 24.

The method further comprises a step (ii) of positioning the needle 4 into the barrel channel 24. As explained above, this step (ii) may occur before or after the step (i) of positioning of the ROM tag 8 onto the needle 4.

The method further comprises a step (iii) of securing the needle 4 inside the barrel channel 24 so that the needle 4 is firmly fixed to the barrel 2. To that end, the gap 240 between an inner wall of the barrel channel 24 and an outer wall of the needle 4 is filled with a glue material. Any glue material usually used to secure a needle into a barrel channel may be used. This step may comprise embedding the ROM tag 8 within the glue material.

The method further comprises a step of writing a Unique Device Identifier (UDI) into the ROM tag 8 for identification of the medical container 1.

The invention claimed is:

1. A medical container comprising a barrel defining a reservoir for containing a medical product, and a needle extending in a barrel channel provided within the barrel at a distal end of the barrel so as to establish a fluid communication between the reservoir and the needle, wherein the medical container further comprises a RFID on-metal (ROM) tag, said RFID on-metal (ROM) tag being located at least partly inside the barrel channel and having an antenna extending along and contacting a needle portion located inside the barrel channel.

2. The medical container according to claim 1, wherein the antenna is spiral-shaped and helically wound up around the needle.

3. The medical container according to claim 1, wherein the RFID on-metal (ROM) tag is an Ultra High Frequency RFID on-metal (UHF-ROM) tag.

4. The medical container according to claim 1, wherein the antenna comprises two separate legs each connected to a chip and forming two non-jointed coils around the needle.

5. The medical container according to claim 1, wherein the medical container comprises an adhesive for securing the needle to the barrel channel, and the RFID on-metal (ROM) tag is embedded into said adhesive.

6. The medical container according to claim 1, wherein the needle portion along which the antenna extends is a predetermined needle portion, said predetermined needle portion having a length of at least 2 mm and said predetermined needle portion corresponding at most to the whole needle portion that is contained inside the barrel channel.

7. The medical container according to claim 1, wherein the antenna is located proximal to a chip of the RFID on-metal (ROM) tag.

8. The method for manufacturing a medical container according to claim 1, comprising the steps of:
   i. positioning the RFID on-metal (ROM) tag onto the needle;
   ii. positioning the needle into the barrel channel;
   iii. securing the needle inside the barrel channel;
      storing a Unique Device Identifier (UDI) into the ROM tag for identification of the medical container.

\* \* \* \* \*